(12) United States Patent
Rheinberger et al.

(10) Patent No.: US 6,479,592 B2
(45) Date of Patent: Nov. 12, 2002

(54) FUNCTIONALIZED AND POLYMERIZABLE POLYMER

(75) Inventors: Volker Rheinberger, Vaduz (LI); Norbert Moszner, Eschen (LI); Franz Stelzer, Graz (AT); Regina Schitter, Murau (AT); Frank Zeuner, Vaduz (LI)

(73) Assignee: Ivoclar Vivadent AG, Liechtenstein (DE)

(*) Notice: Subject to any disclaimer, the term of this patent is extended or adjusted under 35 U.S.C. 154(b) by 0 days.

(21) Appl. No.: 09/377,977

(22) Filed: Aug. 20, 1999

(65) Prior Publication Data

US 2002/0143118 A1 Oct. 3, 2002

Related U.S. Application Data

(63) Continuation of application No. 08/819,504, filed on Mar. 17, 1997, now abandoned.

(30) Foreign Application Priority Data

Mar. 20, 1996 (DE) .......................... 196 13 017
Apr. 12, 1996 (DE) .......................... 196 16 183

(51) Int. Cl.[7] .................... A61K 6/00; C08G 61/00
(52) U.S. Cl. .................... 525/205; 525/207; 525/210; 525/211; 525/227; 526/258; 526/281; 526/282; 526/283; 526/284
(58) Field of Search .................... 526/258, 281, 526/282, 283, 284; 525/205, 207, 210, 211, 227

(56) References Cited

U.S. PATENT DOCUMENTS

| | | | |
|---|---|---|---|
| 3,554,886 A | | 1/1971 | Colomb, Jr. et al. |
| 4,039,491 A | * | 8/1977 | Ikeda et al. |
| 4,054,233 A | | 10/1977 | Cawley |
| 4,872,936 A | | 10/1989 | Engelbrecht |
| 5,491,206 A | * | 2/1996 | Brown-Wensley .......... 526/126 |
| 5,962,703 A | * | 10/1999 | Moszner et al. .............. 106/35 |

FOREIGN PATENT DOCUMENTS

| | | |
|---|---|---|
| EP | 0 219 058 A2 | 4/1987 |
| EP | 0 305 933 A2 | 3/1989 |
| WO | WO 95/07310 | 3/1995 |

OTHER PUBLICATIONS

Bell et al., "A One–Pot Synthesis of Comb Polymers and Hydrogels by the Ring–Opening Metathesis Polymerization Reaction," *Macromolecular Rapid Communications*, 15:543–550 (1994).

Kapellen et al., "Synthesis and Characterization of Amphiphilic Comb–Polymers Via Ring–Opening Metathesis Polymerization of Exo, Exo–5,6–bis (Alkoxymethyl)–7–Oxabicyclo[2.2.1]Hept–2–Enes," *Polymer Bulletin*, 32:3–10 (1994).

Weck et al., "Synthesis of ABA Triblock Copolymers of Norbornenes and 7–Oxanorbornenes via Living Ring–Opening Metathesis Polymerization Using Well–Defined, Bimetallic Ruthenium Catalysts," *Macromolecules*, 29:1789–1793 (1996).

Saunders et al., "Synthesis of Amphiphilic Star Block Copolymers Using Ring–Opening Metathesis Polymerization," *CAPLUS* 1992:152557 (1992).

Naraghi et al., "Recent Developements in the Synthesis of Branched Poly(ethylene oxide)s Via Anionic Polymerization," *CAPLUS* 1997:224424 (1997).

Okoroanyanwu et al., "New Single Layer Positive Photoresists for 193 nm Photolithography," *CAPLUS* 1997:522756 (1997).

Fraser et al., "Synthesis of Glycopolymers of Controlled Molecular Weight by Functional Group Tolerant Ruthenium Carbene Catalysts," *CAPLUS* 1995:806824 (1995).

\* cited by examiner

*Primary Examiner*—Jeffrey Mullis
(74) *Attorney, Agent, or Firm*—Nixon Peabody LLP

(57) ABSTRACT

A functionalized and polymerizable polymer is described which is obtainable by ring-opening metathesis polymerization and is suitable in particular as a dental material and especially as a constituent of dental adhesives owing to an adhesion-boosting effect.

15 Claims, No Drawings

FUNCTIONALIZED AND POLYMERIZABLE POLYMER

This is a continuation of application Ser. No. 08/819,504, filed Mar. 17, 1997, now abandoned.

The invention relates to a functionalized and polymerizable polymer, a process for the preparation thereof, the use thereof and compositions containing the polymer.

Polymers functionalized by carboxyl groups, such as poly(acrylic acid) and poly(methacrylic acid) as well as homo- and copolymers based on maleic acid or fumaric acid, are widely used in technology. They are used, inter alia, as flocculating agents or thickeners, as a component of coatings or adhesives and as a leather or textile auxiliary (cf Ullmann's Encyclopedia of Industrial Chemistry, 5th Ed., Vol. A21, VCH Publisher, Weinheim 1992, page 143 et seq. and Encyclopedia of Polymer Science and Engineering, Vol. 9, Wiley & Sons, New York 1987, page 225 et seq.). Polyacrylic acid is also used in the dental field as a constituent of so-called carboxylate cements or of aluminosilicate-polyacrylic acid cements (cf K. Körber, K. Ludwig, Zahnärztliche Werkstoffkunde und Technologie, Thieme-Verlag, Stuttgart-New York 1982, page 57 et seq.).

Furthermore, in recent years, so-called glass ionomer cements have gained great practical interest. These are cements which are prepared from mixtures of a Ca—Al—F silicate glass powder with an aqueous solution, e.g. of an acrylic acid-maleic acid copolymer. They are used in the dental field as fixing cements, filling materials, base materials, adhesives or fissure sealants (cf A. D. Wilson, J. D. McLean, Glasionomerzement, Quintessens-Verlag, Berlin 1988, page 21 et seq.). In the case of so-called light-curing glass ionomer cements, polymerizable cross-linking monomers and initiators are also added to customary glass ionomer cements, which results in an acceleration of material curing and improvement of the mechanical properties. A further improvement in material properties can be achieved by the use of polycarboxylic acids which bear lateral groups capable of polymerization. Such polycarboxylic acids can be prepared e.g. by polymer-analogous reaction of polyacrylic acid with allyl isocyanate oder 2-isocyanatoethyl methacrylate (cf EP-B-323 120 and S. B. Mitra, Amer. Chem. Soc., Polym. Div., Polym. Prep. 32, (1991) page 517) or e.g. by reaction of oligomaleic acid anhydride with 2-hydroxyethyl methacrylate (cf EP-B-219 058). Corresponding polymers can also be obtained by polymer-analogous reaction of polyacrylic acid with glycidyl methacrylate (cf U.S. Pat. No. 3,872,047). With all these reactions, however, the known disadvantages of polymer-analogous reactions, such as impeded accessibility of the functional groups, non-separability of by-products or the occurrence of ring-closure reactions or crosslinking reactions, have to be accepted (cf M. Fedtke, Reaktionen an Polymeren, Verlag für Grundstoffindustrie, Leipzig 1985, page 17 et seq.).

Furthermore, it is known that mono- or bicyclic alkenes, such as e.g. cyclopentene or norbornene, can be subjected to a ring-opening polymerization with catalysts of olef in metathesis, e.g. $MoO_3/Al_2O_3$ or $WCl_6/(C_2H_5)_3Al$. This type of reaction is also called metathesis polymerization (cf Encyclopedia of Polymer Science and Engineering, Vol. 9, J. Wiley & Sons, New York, 1987, page 634 et seq. and K. J. Ivin, Olef in Metathesis, Academic Press, London 1983).

A ring-opening metathesis polymerization (ROMP) is also possible in the case of polar compounds, such as 7-oxa-bicyclo[2.2.1]hept-5-ene derivatives which have polar substituents in the 2- or 3-position, such as alkoxy, hydroxyalkyl, alkoxycarbonyl, carboxyl or carboxylic acid anhydride, in aqueous-alcoholic reaction medium with ruthenium(III) chloride as catalyst (cf B. M. Novak, R. H. Grubbs, J. Amer. Chem. Soc. 110, (1988) page 960, 7542, W. J. Feast, D. B. Mallison, Polymer 32 (1991) page 558 and A. Y. Lu et al. Makromol. Chem. Phys. 195 (1994) page 1273). Furthermore, the ROMP of cyclooct-5-enyl methacrylate is also known which results in radically crosslinkable polymers (cf B. R. Maughon, R. H. Grubbs, Amer. Chem. Soc., Polym. Div., Polym. Prep. 36, (1995) page 471).

Moreover, bicyclic methacrylates are also known. Thus, U.S. Pat. No. 4,054,233 discloses the synthesis and polymerization of bicyclo[2.2.1]hept-5-en-2-ylmethyl methacrylate in conjunction with peroxidically crosslinkable layers. According to SU-A-1 776 673 and Chem. Abst. 199, 272563, bicyclo[2.2.1]hept-5-en-2-ylmethyl methacrylate or borneol methacrylate is used in the preparation of PVC having improved heat stability. CA-A-1 013 095 discloses adhesive polymers based on reaction products of bicyclo[2.2.1]hept-5-ene-2,3-dicarboxylic acid anhydride with hydroxyalkyl (meth)acrylates, such as 2-hydroxyethyl methacrylate. Radically crosslinkable polyimides which are accessible via 7-oxa-5,6-dicarboxyimid-N-yl-bicyclo[2.2.1]hept-2-ene acrylate are known from T. M. Pyriadi, I. U. Altmamimi, Macromol. Rep. A31, (1994) page 191. Finally, products of the reaction of dicyclopentadiene with (meth)acrylic acid are also known (cf S. Teshigahara, Y. Kano, Toso Kenkyu Hokoko, 35 (1991) page 47 and Chem. Abstr. 116, 84740).

The object of the invention is to make available a functionalized and polymerizable polymer which can be prepared in a simple manner and radically polymerized at room temperature, exhibits good adhesion to various substrates, forms cements with reactive fillers and therefore can be used in particular as a component of cements, coating materials, adhesives or composites and preferably of dental materials. This object is achieved by the functionalized and polymerizable polymer according to Claims 1 and 2.

The subject matter of the present invention is also a process for the preparation of the polymer according to Claim 3, the use thereof according to Claims 4 and 5, and compositions containing the polymer according to Claims 6 to 9.

The functionalized and polymerizable polymer according to the invention is characterized by the fact that it has the following repeat units (IA), (IB) and (IC):

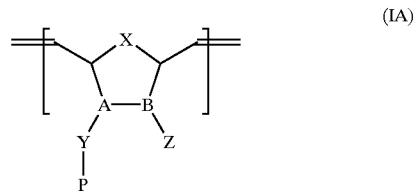

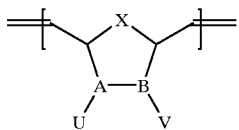

(IB)

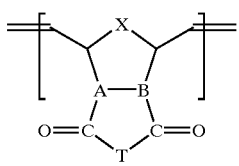

(IC)

where X, A—B, Y, P, Z, U, V, T, $R^1$, $R^2$, $R^3$, $R^4$ and $R^5$ independently of one another have the following meanings:

X=$CH_2$ or O;

A—B=C—C or C=C;

Y=$CH_2O$, CO—O or COO-$R^1$—O, where $R^1$=substituted or unsubstituted $C_1$ to $C_5$ alkylene or oxyalkylene;

P=a polymerizable group, namely $CH_2$=CH—CO—, $CH_2$=C($CH_3$)—CO—, $CH_2$=CH—$CH_2$— or $CH_2$=CH—$C_6H_5$—$CH_2$—;

Z=H, COOH, substituted or unsubstituted $C_1$ to $C_{12}$ alkyl or $COOR^4$, where $R^4$=substituted or unsubstituted $C_1$ to $C_{12}$ alkyl or $C_6$ to $C_{14}$ aryl, U=COOH or $COOR^5$, where $R^5$=substituted or unsubstituted $C_1$ to $C_{12}$ alkyl or $C_6$ to $C_{14}$ aryl;

V=H, COOH, $CH_2$—OH, $OR^2$ or CO—$OR^2$, where R=substituted or unsubstituted $C_1$ to $C_{12}$ alkyl or $C_6$ to $C_{14}$ aryl; and T=O, NH or $NHR^3$, where $R^3$=substituted or unsubstituted $C_1$ to $C_{12}$ alkyl or $C_6$ to $C_{14}$ aryl; and where the mole fraction a of the unit (IA), the mole fraction b of the unit (IB) and the mole fraction c of the unit (IC) are as follows:

a=0.05 to 1.0;
b=0 to 0.95; and
c=0 to 0.90.

The polymer is preferably built up from the units (IA) and optionally (ID) and optionally (IC).

Furthermore, A—B and X are also chosen independently of one another in the individual five-membered rings.

The alkyl and aryl groups of Z, $R^1$, $R^2$, $R^3$, $R^4$ and $R^5$ can optionally be substituted by one or more simple functional groups, in particular COOH, OH, $C_1$ to $C_6$ alkoxy or halogen.

For simplication, the polymer according to the invention is in the following represented by the general formula (I):

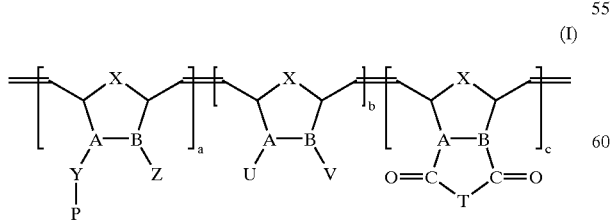

(I)

The type of simplifying representation chosen in formula (I) is also used analogously for other compounds in the description and in the claims.

Preferred definitions which can be chosen independently of one another exist for the above-mentioned variables of the polymer according to the invention, these definitions being as follows:

X=$CH_2$ or O;

A—B=C—C;

Y=$CH_2O$ or CO—O—$R^1$—O;

$R^1$=$CH_2CH_2$ or $CH_2$—CHOH—$CH_2$;

P=$CH_2$=C($CH_3$)—CO;

Z=H or COOH;

$R^4$=$CH_3$, $C_2H_5$ or phenyl;

U=COOH;

$R^5$=$CH_3$, $C_2H_5$ or phenyl;

V=H or COOH;

$R^2$=$CH_3$ or $C_2H_5$;

T=O;

$R^3$=$CH_3$ or phenyl;

a=0.10 to 0.80;

b=0 to 0.80, in particular more than 0 and up to 0.80; and/or c=0 to 0.60, in particular more than 0 and up to 0.60.

Preferred compounds are accordingly those in which at least one of the variables of the formula (I) has the preferred definition described above.

In order to prepare the polymer according to the invention, the bicyclic compound (II) or optionally mixtures of (II) with the bicyclic compound (III) and/or the bicyclic compound (IV) are subjected to a ring-opening metathesis polymerization in the presence of a catalyst, and protective groups present are then cleaved off when protected educts are used. After the metathesis polymerization, the positions of A and B with the radicals bound thereto are no longer distinguishable from one another. Instead of (II), (III) and (IV), those compounds in which only the positions of A and B with the radicals bound thereto are exchanged can also be used as educts.

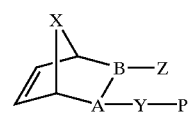

(II)

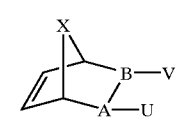

(III)

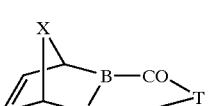

(IV)

Examples of suitable protective groups are trimethylsilyl groups and tetrahydropyranyl groups.

In addition, the polymer (I) according to the invention is also obtainable by polymer-analogous reaction of the polymer (V) with the polymerizable educt P-halogen, in accordance with the reaction equation below:

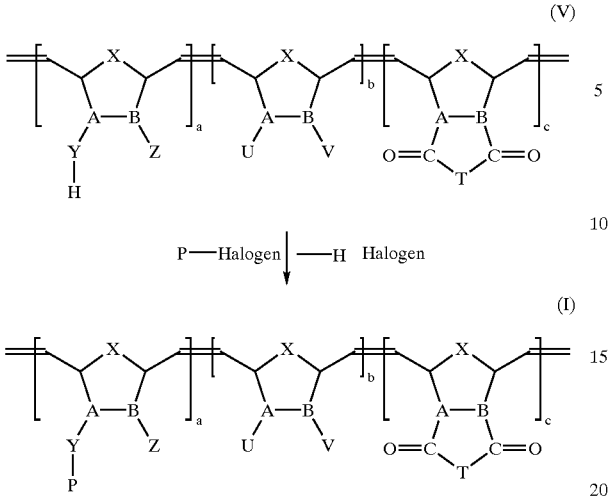

(V)

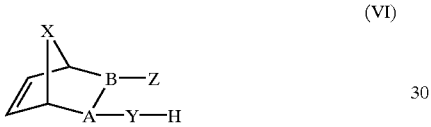

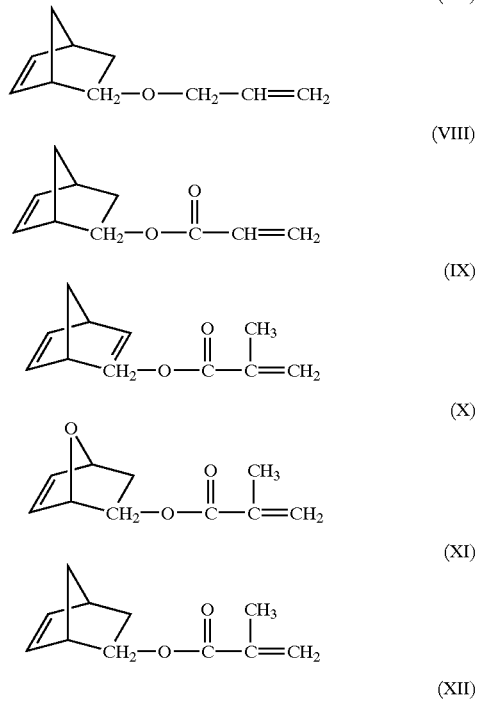

(I)

The polymer (V) can be prepared in the presence of a suitable catalyst by ring-opening metathesis polymerization of a mixture of the bicyclic compound (VI) with the bicyclic compound (III) and the bicyclic compound (IV).

(VI)

It is known that catalyst systems based on compounds of the transition metals of the IVth to VIIIth sub-group can be used as catalysts for ring-opening metathesis polymerization (ROMP) (cf Encyclopedia of Polymer Science and Engineering, Vol. 9, J. Wiley & Sons, New York 1987, page 648 et seq.).

Above all, compounds of Mo, W, Ru, Os and Ir are used. Customary catalysts are based on metal carbene complexes, such as Ru, W or Mo carbene complexes (cf R. R. Schrock, Acc. Chem. Res. 23 (1990) 158). Simple salts such as $K_2RuCl_5$ or the hydrates of $RuCl_3$ or $OsCl_3$ are suitable in particular for the ring-opening metathesis polymerization of polar monomers (W. J. Feast, D. B. Harrison, Polymer 32 (1991) 558). Various solvents can be used depending on the catalyst used. Thus, e.g. in the case of metal carbene complexes, aprotic solvents such as THF, benzene, chlorobenzene, toluene, pentane or dichloromethane are used, whereas with $RuCl_3$ the ring-opening metathesis polymerization is usually carried out in an aqueous-alcoholic medium. The use of 1-alkenes, cis-2-butene-1,4-diol or acrylic acid in particular is suitable for controlling the molecular weight of the polymers obtained. The temperature at which the polymerization is carried out is normally in the range from 15–60° C. when metal carbenes are used as catalyst, and from 40 to 70° C. in the case of e.g. $RuCl_3$.

The bicyclic compounds of the formulae (II), (III), (IV) and (VI) which are used as educts for the preparation of the polymer according to the invention are known or can be prepared in a simple manner by known methods.

Representatives of the general formula (II) are e.g. bicyclo[2.2.1]hept-5-en-2-ylmethylallyl ether (VII), bicyclo[2.2.1]hept-5-en-2-ylmethyl acrylate (VIII), bicyclo[2.2.1]hept-2,5-dien-2-ylmethyl methacrylate (IX), 7-oxabicyclo[2.2.1]hept-5-en-2-ylmethyl methacrylate (X), bicyclo[2.2.1]hept-5-en-2-ylmethyl methacrylate (XI) or the 1:1 reaction product (XII) of bicyclo[2.2.1]hept-5-ene-2,3-dicarboxylic acid anhydride and 2-hydroxyethyl methacrylate, where (XI) and (XII) are known.

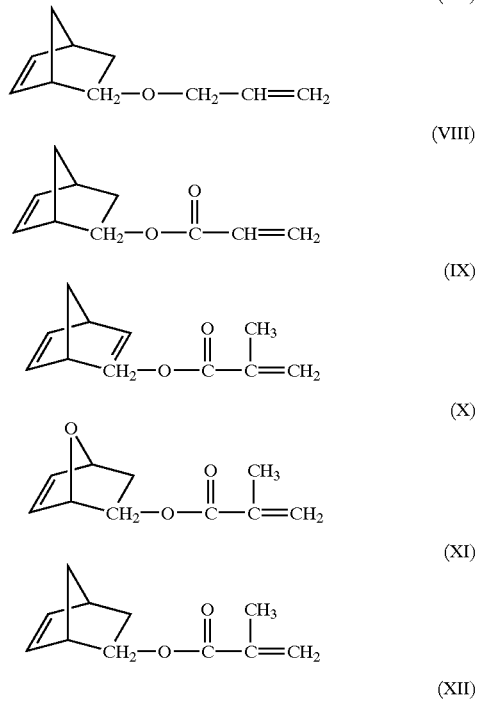

Representatives of the general formula (III) are e.g. bicyclo[2.2.1]hept-5-ene-2-carboxylic acid (XIII), bicyclo[2.2.1]hept-5-ene-2,3-dicarboxylic acid monomethyl ester (XIV), bicyclo[2.2.1]hept-2,5-diene-2,3-dicarboxylic acid (XV), bicyclo[2.2.1]hept-5-ene-2,3-dicarboxylic acid (XVI) or 7-oxabicyclo[2.2.1]hept-5-ene-2,3-dicarboxylic acid (XVII), where (XVI) and (XVII) are known.

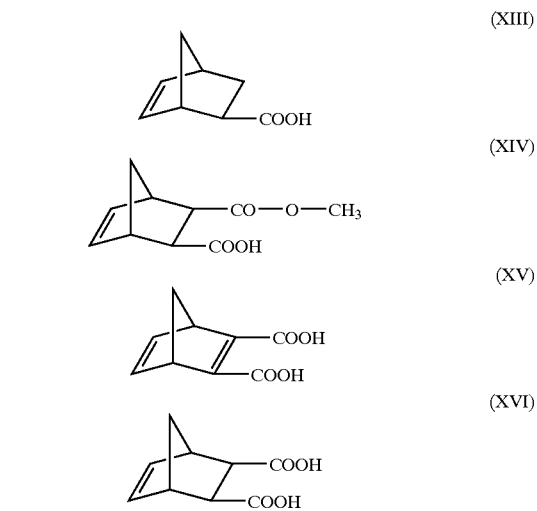

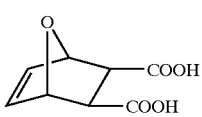 (XVII)

Representatives of the general formula (IV) are e.g. bicyclo[2.2.1]hept-5-ene-2,3-dicarboxylic acid imide (XVIII), bicyclo[2.2.1]hept-2,5-diene-2,3-dicarboxylic acid anhydride (XIX), bicyclo[2.2.1]hept-2,5-diene-2,3-dicarboxylic acid-N-phenylimide (XX), bicyclo[2.2.1]hept-5-ene-2,3-dicarboxylic acid anhydride (XXI) or 7-oxabicyclo[2.2.1]hept-5-ene-2,3-dicarboxylic acid anhydride (XXII), where (XXI) and (XXII) (cf O. Diels, K. Alder, Chem. Ber. 62, (1929) page 557) are known.

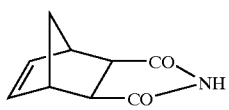 (XVIII)

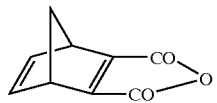 (XIX)

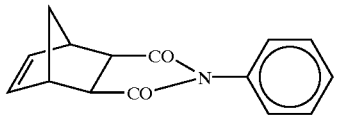 (XX)

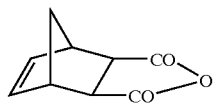 (XXI)

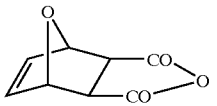 (XXII)

Representatives of the general formula (VI) are e.g. 7-oxabicyclo[2.2.1]hept-5-ene-2-carboxylic acid (XXIII), 7-oxabicyclo[2.2.1]hept-2,5-diene-2-carboxylic acid (XXIV), bicyclo[2.2.1]hept-5-ene-2-carboxylic acid-2-hydroxyethyl ester (XXV), bicyclo[2.2.1]hept-5-ene-2-methanol (XXVI) or bicyclo[2.2.1]hept-5-ene-2-carboxylic acid (XIII), where (XXVI) and (XIII) are known.

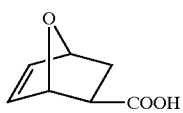 (XXIII)

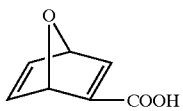 (XXIV)

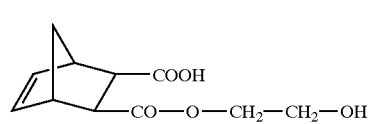 (XXV)

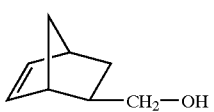 (XXVI)

The bicyclic compounds of the formulae (II) to (IV) and those of the formula (VI) can be prepared in a simple manner by way of a Diels-Alder reaction (cf H. Wollweber, Diels-Alder-Reaktion, G. Thieme-Verlag 1972) of cyclopentadiene or furan with suitable dienophiles, such as maleic acids acetylene dicarboxylic acid or acrylic acids or derivatives thereof, and optionally subsequent modification of the obtained bicyclic compounds, e.g. by reduction, hydrolysis, etherification or esterification. Thus, e.g. the compound (VII) can be synthesized by way of a Diels-Alder reaction of cyclopentadiene with acrylic acid methyl ester, subsequent reduction of the bicyclic adduct to 5-norbornene-2-methanol (XXVI) and etherification thereof with allyl bromide.

Special polymers according to the invention can be prepared in particular by ring-opening metathesis copolymerization of the known bicyclo[2.2.1]hept-5-en-2-ylmethyl methacrylate (XI) with a trimethylsilyl- or tetrahydropyranyl-protected, commercial bicyclo[2.2.1]hept-5-ene-2,3-dicarboxylic acid in the presence of a suitable molybdenum-carbene catalyst and subsequent removal of protective groups by acid hydrolysis. In an analogous manner, polymers according to the invention can also be obtained by copolymerization of 7-oxabicyclo[2.2.1]hept-5-en-2-ylmethyl methacrylate (X) with the known 7-oxabicyclo[2.2.1]hept-5-ene-2,3-dicarboxylic acid anhydride (XXII) in the presence of ruthenium(III) chloride in aqueous-alcoholic medium.

The polymer according to the invention is suitable in particular as constituent of cements, coating materials and composites, and in particular of adhesives. The polymer according to the invention is particularly preferably used as a dental material or a constituent of dental material, in particular as a constituent of dental adhesives. Its ability on the one hand to form a bond with the material to be fixed e.g. a composite material via existing polymerizable groups such as (meth)acrylate groups, and on the other hand to develop an adhesion-promoting interaction with the substrate such as in particular the dentine via carboxyl groups, proves to be advantageous.

When the polymer according to the invention is used as a constituent of dental materials, it is normally used in a quantity of 0.1 to 60, in particular 1.0 to 40, wt. %, relative to the dental material. In order to prepare the dental materials, the polymer according to the invention is in particular combined with polymerizable organic binders, cross-linking monomers, fillers, reactive fillers, polymerization initiators and/or further additives, such as customary stabilizers, e.g. hydroquinone monomethyl ether (MEHQ) or 2,6-di-tert.-butyl-4-methylphenol (BHT), UV absorbers, pigments, dyes or solvents.

Suitable as polymerizable organic binders are all binders which can be used for a dental material, in particular monofunctional or polyfunctional (meth)acrylates which can be used singly or as mixtures. Preferred examples of these compounds are methyl (meth)acrylate, isobutyl (meth)acrylate, cyclohexyl (meth)acrylate, tetraethylene glycol di(meth)acrylate, triethylene glycol di(meth)acrylate, diethylene glycol di(meth)acrylate, ethylene glycol di(meth)acrylate, polyethylene glycol di(meth)acrylate, butanediol di(meth)acrylate, hexanediol di(meth)acrylate, decanediol di(meth)acrylate, dodecanediol di(meth)acrylate, bisphenol-A-di(meth)acrylate, trimethylolpropane tri(meth)acrylate, 2,2-bis-4-(3-methacryloxy-2-hydroxypropoxy)-phenylpropane (bis-GMA) and the products of the reaction of isocyanates, in particular di- and/or triisocyanates, with OH group-containing (meth)acrylates. Particularly preferred examples of the last-mentioned products are obtainable by reaction of 1 mol of hexamethylene diisocyanate with 2 mol of 2-hydroxyethylene methacrylate, of 1 mol of tri-(6-isocyanatohexyl)biuret with 3 mol of 2-hydroxyethyl methacrylate and of 1 mol of 2,2,4-trimethylhexamethylene diisocyanate with 2 mol of 2-hydroxyethyl methacrylate.

The organic binders are normally used in the dental material according to the invention in a quantity of 0 to 90 wt. %.

Suitable as cross-linking monomers are in particular the above-named polyfunctional (meth)acrylates, in particular triethylene glycol di(meth)acrylate, polyethylene glycol di(meth)acrylate, bis-GMA or urethane di(meth)acrylates.

The cross-linking monomers are normally used in the dental material according to the invention in a quantity of 0 to 80 wt. %.

Examples of preferred fillers are quartz powder, glass ceramic powder and glass powder, in particular of barium silicate glasses, Li/Al silicate glasses and barium glasses, aluminas or silicas, very finely divided silicas, in particular pyrogenic or precipitated silicas, X-ray-opaque fillers such as ytterbium trifluoride.

The fillers are typically used in a quantity of 0 to 85 wt. %, relative to the dental material.

Above all, fluoroaluminosilicate glasses and other glasses used in glass ionomer cements come into consideration as reactive fillers. The reactive fillers are normally used in the dental material according to the invention in a quantity of 0 to 80 wt. %.

Particularly preferred dental materials according to the invention are light-curing glass ionomer cements, dentine adhesives and compomers.

Quite particularly advantageous glass ionomer cements, dentine adhesives and compomers and the respective components thereof are given below:

Light-curing Glass Ionomer Cements:

- polymer according to the invention,
- reactive glass powder, in particular customary fluoroaluminosilicate glasses with an average particle size of about 0.05 to 15 µm (cf A. D. Wilson, J. W. McLean, Glasionomerzement, Quintessenz Verlags-GmbH, Berlin 1988, page 21 et seq.),
- polymers with carboxyl groups, e.g. acrylic acid or maleic acid polymers, which optionally bear laterally bound groups capable of polymerization, e.g. (meth)acrylate groups,
- photoinitiators and stabilizers,
- $H_2O$, and
- cross-linking monomers.

Dentine Adhesives:

- polymer according to the invention,
- hydrophilic monomers, such as 2-hydroxyethyl (meth)acrylate or 2-hydroxypropyl (meth)acrylate or polyethylene glycol mono- or dimethacrylates or n-vinyl pyrrolidone,
- carboxylic or phosphoric acids capable of polymerization, such as e.g. maleic acid or 2-(meth)acryloyloxyethyl dihydrogenphosphate,
- cross-linking monomers,
- water, alcohol or acetone and
- photoinitiators and stabilizers.

Compomers:

- polymer according to the invention,
- glass powder, in particular fluoroaluminosilicate glasses customary for glass ionomer cements, with an average particle size of about 0.05 to 5 µm (cf A. D. Wilson, J. W. McLean, Glasionomerzement, Quintessenz Verlags-GmbH, Berlin 1988, page 21 et seq.),
- photoinitiators and stabilizers,
- customary cross-linking monomers,
- cross-linking monomers containing carboxyl groups, such as the reaction products of 2 mol of 2-hydroxyethyl (meth)acrylate or 2-hydroxypropyl (meth)acrylate with 1 mol of 5-(2,5-dioxotetrahydrofuryl)-3-methylcyclohex-3-ene-1,2-dicarboxylic acid anhydride or the dianhydrides of e.g. commercial tetrahydrofuran-2,3,4,5-tetracarboxylic acid, of cyclohexane-1,2,3,4,5,6-hexacarboxylic acid or of butane-1,2,3,4-tetracarboxylic acid, and corresponding reaction products of these multifunctional carboxylic acids with more than 1 mol of glycidyl methacrylate.

The dental materials according to the invention and the polymers according to the invention can be polymerized by heat, in the cold or by light. The known peroxides such as dibenzoyl peroxide, dilauroyl peroxide, tert.-butylperoctoate or tert.-butylperbenzoate can be used as initiators for hot polymerization. Moreover, 2,2'-azoisobutyric acid nitrile (AIBN), benzpinacol and 2,2'-dialkylbenzpinacols are also suitable.

For example, benzophenone and derivatives thereof as well as benzoin and derivatives thereof can be used as initiators for photopolymerization. Further preferred photoinitiators are the α-diketones, such as 9,10-phenanthrenequinone, diacetyl, furil, anisil, 4,4'-dichlorobenzil and 4,4'-dialkoxybenzil. Camphor quinone is particularly preferably used. Moreover, the group of acyl phosphine oxides is also highly suitable for the initiation of photopolymerization. In order to accelerate the initiation, the photoinitiators are used preferably together with a reducing agent, particularly preferably with an amine, in particular an aromatic amine.

Radical-supplying redox systems, for example benzoyl or lauroyl peroxide together with amines such as N,N-dimethyl-p-toluidine, N,N-dihydroxyethyl-p-toluidine or other structurally related amines are used as initiators for cold polymerization.

The combination of photoinitiators with different redox systems has proved effective especially in the case of dental materials for the cementing of dental restorations, such as glass ceramic inlays, onlays, part-crowns and crowns. Combinations of camphor quinone, benzoyl peroxide and amines such as N,N-dimethyl-p-toluidine and/or N,N-cyanoethylmethylaniline are preferred.

The concentration of the initiators preferably lies in the range from 0.05 to 2.0 wt. %, particularly preferably in the range from 0.1 to 0.8 wt. %, relative to the dental material.

The invention is explained in more detail below with reference to examples.

EXAMPLES

Example 1

Methacrylic Acid-(5-Norbornene-2-endo/exo-methyl)ester (1)

31.7 g (0.25 mol) of 2-(hydroxymethyl)-5-norbornene (mixture of endo-/exo-isomers), 400 ml of dried tetrahydrofuran (THF), 26.8 g (0.27 mol) of freshly distilled triethylamine (TEA) and 0.01 g of 2,6-di-tert.-butyl cresol (BHT) are introduced under argon into a 1500 ml sulphonation flask with a mechanical stirrer, 150 ml dropping funnel and thermometer at 0° C. accompanied by stirring. A solution of 29.5 g (0.28 mol) of methacrylic acid chloride in 100 ml of THF is slowly added dropwise such that the temperature remains between 0° C. and 5° C. The reaction mixture is then allowed to warm up to room temperature over a period of 60 minutes, accompanied by further stirring. The mixture is then filtered with suction, and the residue filtered off is washed with 150–200 ml of diethyl ether. The filtrate is extracted with 150 ml of a saturated NaCl solution, which is adjusted to a pH of 1–2 with concentrated HCl. The combined organic phases are then washed neutral with 2×100 ml of saturated NaCl solution, and subsequently extracted with 150 ml of a saturated NaCl solution made basic with 50 ml of 10% $Na_2CO_3$ solution. Finally the organic phase is washed neutral with 2×100 ml of saturated NaCl solution, dried for 20 minutes with 50 g of anhydrous $Na_2SO_4$ accompanied by stirring, filtered and concentrated at 30° C. in a rotary evaporator. The residue obtained is distilled over a period of 35 minutes under a medium high vacuum (0.02 mbar) at a bath temperature of about 110° C., whereby 23.5 g (55% yield) of a colourless liquid (b.p.$_{0.02\ mbar}$=70–74° C.) is obtained.

Elemental analysis: $C_{12}H_{16}O_2$: Calc.: C, 74.96 H, 8.39. (192.25) Found: C, 74.44 H, 8.33. $^1$H-NMR (90 MHz, CDCl$_3$): 0.56 and 0.72 (m, 1H, C$\underline{H}$—CH$_2$O); 1.25–1.60 (m, 2H, C$\underline{H}$—CH—CH$_2$O); 1.70–1.95 and 2.41–2.7 (m, 2×1H, CH-norbornene); 2.00 (s, 3H, CH$_3$); 2.75–3.0 (b, 2H, CH$_2$-norbornene); 3.65–4.30 (m, 2H, CH$_2$O); 5.60 and 6.18 (s, 2×1H, CH$_2$=)); 5.95–6.14 and 6.17–6.30 (m, 2×1H, CH=CH, overlapped by CH$_2$=); IR (Film, cm$^{-1}$): 1719 (C=O); 1636(C=C)

Example 2

7-Oxabicyclo[2.2.1]hept-5-ene-2,3-endo/exo-dicarboxylic Acid bis(Trimethylsilyl)ether (2)

14.8 g (0.1 mol) of 7-oxabicyclo[2.2.1]hept-5-ene-2,3-endo/exo-dicarboxylic acid are dissolved in 150 ml of dried THF in a 500 ml sulphonation flask with a mechanical stirrer, dropping funnel and thermometer. The apparatus is flushed with argon, and the mixture introduced is cooled to 10–15° C. accompanied by stirring. 20.2 g (0.2 mol) of TEA and 21.7 g (0.2 mol) of trimethylsilyl chloride are then added dropwise. In order to complete the reaction, stirring is continued for a further 3 hours. The formed precipitate of TEA hydrochloride is filtered off by suction under argon, washed with THF, and the combined organic phases are concentrated in a rotary evaporator at 30–40° C. After drying under a medium high vacuum, about 32 g of a colourless oil are obtained, which becomes solid after cooling in a deep freezer. Purification is accomplished by recrystallation from 900 ml of anhydrous petroleum ether and drying under a medium high vacuum. 18.6 g (58% yield) of colourless crystals are obtained (melting point: 65–70° C.).

Elemental analysis: $C_{14}H_{24}O_5Si_2$ Calc.: C, 51.18 H, 7.36. (328.50) Found: C, 50.90 H, 6.18. $^1$H-NMR (90 MHz, CDCl$_3$): 0.26 (s, 18H, CH$_3$Si); 2.78 (d, 3H, CHCOO-exo); 3.34 (m, 7H, CHCOO-endo); 5.10 (b, 7H, CHOCH-endo); 5.22 (b, 3H, CHOCH-exo); 6.48 (s, 3H, CH=CH-exo); 6.55 (s, 7H, CH=CH-endo), $^{13}$C-NMR (75 MHz, CDCl$_3$): 0.02 (CH$_3$ ↑); 47.7 and 49.5 (CH—C=O ↑); 80.4 (C—O—C ↑); 135.1 and 135.5 (C=C ↑); 170.8 and 175.3 (C=O (-)).

Example 3

Bicyclo[2.2.1]hept-5-ene-2,3-endo/exo-dicarboxylic acid bis(Tetrahydropyran-2-yl)ester (3)

21.2 g (0.25 mol) of 3,4-dihydro-2H-pyran (DHP) are added at room temperature to a solution of 18.2 g (0.10 mol) of 5-norbornene-2,3-endo/exo-dicarboxylic acid and 1.5 g (6 mmol) of pyridinium tosylate in 100 ml of absolute dichloromethane, and the mixture is stirred for 42 hours. The yellowish solution formed is shaken out with 2×50 ml of saturated NaHCO$_3$ solution. The organic phase obtained is dried over anhydrous Na$_2$SO$_4$ and filtered off by suction through a layer of basic Al$_2$O$_3$. Finally, the solvent and excess DHP are drawn off in a rotary evaporator. The remaining oil is dissolved in 200 ml of hexane at 50° C., and filtered again through a layer of basic Al$_2$O$_3$. After concentration of the filtered hexane solution to about 70 ml and cooling, about 25 g (71% yield) of colourless crystals are precipitated (melting point: 82–96° C.).

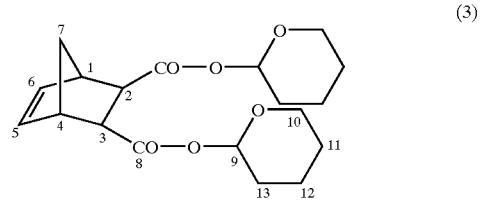

(3)

$^1$H-NMR (300 MHz, CDCl$_3$): 1.40–1.90 (14H, m, H7, H11, H12, H13), 2.26 (1H, dd, H2), 3.20 (1H, br. s, H1), 3.33 (1H, br. s, H4), 3.46 (1H, m, H3), 3.70 (2H, m, H10), 3.85 (2H, m, H10), 5.95 (1H, br. s, H9), 6.02 (1H, br. s, H9), 6.13 (1H, m, H5) and 6.33 (1H, dd, H6); $^{13}$C-NMR (75 MHz, CDCl$_3$): 18.6, 25.2, 25.5, 31.3 (C11, C12, C13), 46.0 (C4), 47.0–48.4 (C1, C2, C3, C7), 63.1 (C10), 93.0 (C9), 135.2 (C5), 137.6 (C6), 171.8, 173.1 and 179.3 (C=O).

Example 4

Synthesis of a Molybdenum-carbene Complex Which can be Used as a Catalyst (Analogous to: R. R. Schrock et al., J. Amer. Chem. Soc. 112, (1990) 3875)

The catalyst described in this example has the structural formula below and is in the following referred to as catalyst HF.

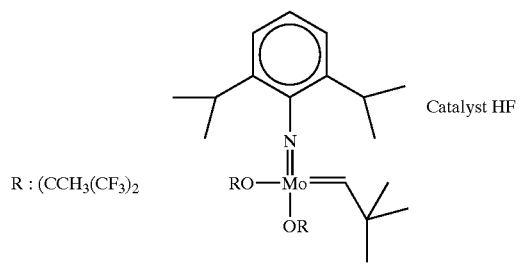

Catalyst HF 2.22 g (11.8 mmol) of lithium-tert.-1,1,1,3,3,3-hexafluorobutoxide are slowly added as a solid at −30° C. to a solution of 4.0 g (5.5 mmol) of Mo(CHCMe$_3$)(NAr)(OSO$_2$CF$_3$)$_2$(dme) (Ar=2,6-diisopropylphenyl, dme=ethylene glycol dimethyl ether) in a mixture of 200 ml of diethyl ether and 200 ml of ethylene glycol dimethyl ether over a period of 10 minutes. The reaction mixture is then brought to room temperature, stirred for 2 hours and concentrated until dry. The dark orange solid is extracted with about 50 ml of pentane, filtered through a layer of Celite® and concentrated. The residue is recrystallized from pentane. The catalyst HF obtained can be used for ring-opening metathesis polymerization.

$^1$H-NMR (300 MHz, CDCl$_3$): 1.04 (s, 1H, MoCHCMe$_3$), 1.16 (d, 12H, CH(C$\underline{H}_3$)$_2$), 1.37 (s, 6H, OCMe(CF$_3$)$_2$), 3.54 (sept, 2H, CHMe$_2$), 6.94 (m, 3H, NAr) and 12.06 (s, 1H, MoCHCMe$_3$).

Example 5

(A:) General Instructions for Ring-opening Metathesis Polymerization with Metal-carbene Catalysts for the Synthesis of the Polymers According to the Invention:

The ring-opening metathesis polymerization using transition metal carbene complexes is carried out in an inert gas atmosphere in absolute aprotic solvents such as chlorobenzene, benzene, toluene, THF or dichloromethane, using 1-alkenes, e.g. 1-hexene, as chain-transfer agents for controlling the molecular mass.

Thus 1–25 parts by weight of chain-transfer agent and a 10 wt. % solution of 1 part by weight of catalyst are added, accompanied by stirring, to a 10–20 wt. % solution of 100–1000 parts by weight of monomer. Polymerization is carried out at room temperature. After polymerization is complete, the reaction is terminated with benzaldehyde, and the polymer is precipitated in methanol and purified by reprecipitation.

(B:) Synthesis of the Copolymer (4) According to the Invention 8.00 g (22.8 mmol) of monomer (3) (cf Example 3) and 1.10 g (5.7 mmol) of monomer (1) (cf Example 1) are dissolved under inert gas atmosphere together with 25 mg (0.30 mol) of 1-hexene in 40 ml of chlorobenzene. A solution of 30 mg (0.043 mmol) of catalyst HF is added to this solution accompanied by stirring. After 4 hours, the polymerization is terminated with about 0.3 ml of benzaldehyde, and the polymer obtained is precipitated in 300 ml of ethanol stabilized with BHT (100 ppm), and then dried. The polymer is dissolved in THF to remove the THP protective group, and the solution formed is added dropwise into a hot solution of about 50 mg of p-toluenesulphonic acid in 30 ml of stabilized ethanol so slowly that the cloudiness forming in each case dissolves. Stirring is continued for 20 minutes, and the polymer (4) soluble in ethanol is precipitated from a mixture of pentane/diethyl ether (2/1 parts by volume). The polymer obtained is finally dried under a medium high vacuum with protection from light, and its number average molecular weight is measured as ($M_n$=13,500 g/mol). The molecular weight was determined by means of gel permeation chromatography (GPC), calibration being carried out with polystyrene standards.

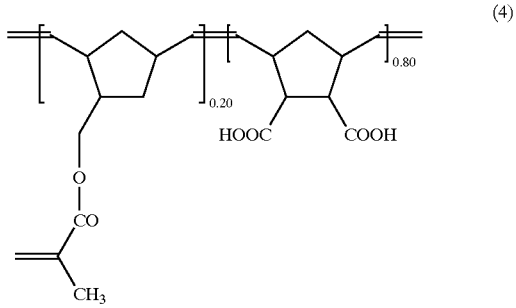

(4)

Example 6

Synthesis of the Terpolymer (5) According to the Invention

In an analogous manner to Example 5, a solution of 23.2 mg (0.033 mmol) of catalyst HF in 2 ml of methylene chloride is added to a solution of 2.63 g (7.5 mmol) of monomer (3), 0.29 g (1.5 mmol) of monomer (1), 0.24 g (1.0 mmol) of bicyclo[2.2.1]hept-5-ene-2,3-exo/endo-dicarboxylic acid-N-phenylimide, which is readily accessible by Diels-Alder reaction of cyclopentadiene and N-phenylmaleinimide, and 6.1 mg (0.072 mmol) of 1-hexene in 8 ml of methylene chloride. The polymerization solution quickly becomes highly viscous. After 2 hours, the polymerization is discontinued by adding the polymerization solution dropwise to about 100 ml of ethanol. The precipitated polymer is filtered off and dried and exhibits a number average molecular mass (GPC, calibration with polystyrene standards) of 31,000 g/mol. To cleave off the THP protective group, the polymer is dissolved in 10 ml of THF and the solution is added dropwise to a solution, at 50° C., of 30 mg of p-toluenesulphonic acid in 50 ml of ethanol so slowly that the precipitate formed dissolves. 1.3 g (68% yield) of terpolymer (5) are finally obtained by adding the obtained polymer solution dropwise to 400 ml of diethyl ether and drying the obtained residue in vacuo. The number average molecular mass determined by GPC is 14,000 g/mol, the $^1$H-NMR spectrum indicating that the composition of the terpolymer corresponds to the composition of the monomer mixture used.

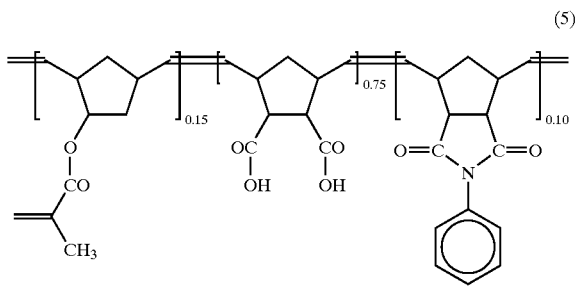

(5)

Example 7

Synthesis of Polymers According to the Invention by Ring-opening Metathesis Polymerization of Monomer (3) and Subsequent Polymer-analoqous Reaction with GMA Rinq-opening Metathesis Polymerization:

In a manner analogous to that of Example 5, a solution of 50 mg of catalyst HF in 2 ml of chlorobenzene is added to a solution of 23 g of monomer (3) and 153 mg of 1-hexene in 80 ml of chlorobenzene. After 2 hours, the same quantity of catalyst solution is added again. After 4 hours, the polymerization is discontinued. The polymerization solution is diluted with 300 ml of ethanol and, after 50 mg of p-toluenesulphonic acid has been added, is heated under reflux for 30 minutes to cleave off the protective group. The solution obtained is then concentrated in vacuo until almost dry. The resulting residue is dissolved in THF, and the THF solution is added dropwise to 200 ml of diethyl ether, whereupon a precipitate forms. After separation and drying under a medium high vacuum, about 11 g (92% yield) of polymer (6) are obtained with a number average molecular mass of 1200 g/mol (gel permeation chromatography (GPC)—with polystyrene standard).

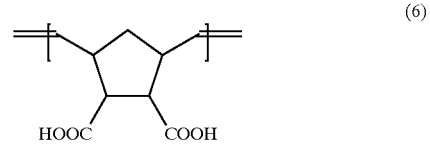

(6)

Polymer-analogous Reaction with Glycidyl Methacrylate (GMA):

1.55 g (10.9 mmol) of GMA, 11.6 mg (0.11 mmol) of lithium perchlorate as catalyst and a spatula tip of hydroquinone monomethyl ether (MeHQ) are added to a solution of 5 g (27.2 mmol) of polymer (6) in 20 ml of sec. butanol. The reaction mixture is stirred for 24 hours at 60° C. The reaction product is then precipitated by introducing the mixture into 150 ml of ethyl acetate, dissolved in methanol and precipitated again by adding the obtained solution dropwise to ethyl acetate, and finally dried under a medium high vacuum. 3.8 g of polymer (7) are obtained, the structure being confirmed by means of titration of the free carboxyl groups and by $^1$H-NMR spectroscopy.

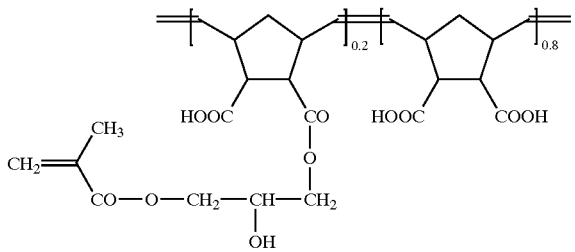

(7)

Example 8

Dentine Adhesive Based on Copolymer (4)

A 1-Component Dentine Adhesive of the Following Composition is Prepared Based on Copolymer (4):

copolymer (4): 18.0 wt. % water, deionized: 32.4 wt. %

2-hydroxyethyl methacrylate: 44.2 wt. % maleic acid: 3.0 wt. % camphor quinone: 0.3 wt. %

MeHQ: 0.1 wt. % ammonium fluoride: 1.0 wt. % diphenyliodonium hexafluorophosphate: 1.0 wt. %

In order to determine the shear adhesion that can be attained with this dentine adhesive, dentine surfaces of extracted, embedded teeth were initially ground flat with 500- and 1000-grade abrasive paper. The dentine surfaces were then lightly dried with cellulose. The dentine adhesive was applied to the surfaces in 2 layers, dried with compressed air and irradiated with a Heliolux GTE (Vivadent) dental light source. A commercially obtainable filling composite, namely Compoglass from Vivadent, Liechtenstein, was then applied in 2 layers and irradiated for 40 seconds in each case. The test specimens obtained were then placed in distilled water and stored there for 24 hours at 37° C. Shear adhesion was finally determined according to ISO proposal ISO-TR 11405: "Dental material—Guidance on testing of adhesion to tooth structure", as 15.6±7.8 MPa. An analogous formulation in which the polymer (4) was replaced by conventional polyacrylic acid, namely Plex 4779 from Röhm, gave only values of 3.9±0.6 MPa.

Example 9

Light-curing Glass Ionomer Cement Based on Copolymer (4)

Liquid 1:

urethane dimethacrylate[1]: 56.5 wt. %

2-hydroxyethyl methacrylate: 18.8 wt. %

PEG-600 dimethacrylate: 18.8 wt. %

1% aqueous solution of p-toluenesulphonic acid: 5.1 wt. %

2-cyanoethylmethylaniline: 0.5 wt. % camphor quinone: 0.3 wt. %

Powder 2:

reactive glass powder[2]: 92.5 wt. % copolymer (4): 6.0 wt. %

L(+)-tartaric acid: 1.5 wt. %

1) urethane dimethacrylate made from 2 mol of 2-hydroxyethyl methacrylate and 1 mol of 2,2,4-trimethylhexamethylene diisocyanate-1,6.
2) glass composition (according to atomic absorption spectrometry and titration for fluoride determination) (wt. %): $SiO_2$: 25.5, $Al_2O_3$: 23.8, $Na_2O$: 1.8, CaO: 16.4, $P_2O_5$: 8.2, BaO: 11.2 and fluoride: 17.0; average particle size 8 μm.

A mixture is prepared from in each case one part by weight of liquid 1 and powder 2. Test specimens are prepared with the material and are stored in $H_2O$ for 2 hours at 37° C., and subsequently irradiated twice for 90 seconds by means of a dental radiation source, Spectramat (Vivadent). The compressive strength determined according to ISO standard 9917 (Dental water-based cements) is 128.4 MPa, compared with 117.1 MPa for a material in which the copolymer (4) in the powder was replaced by the same proportion of polyacrylic acid-Plex 4779.

What is claimed is:

1. Functionalized and polymerizable polymer, which contains the following repeat units (IA), (IB) and (IC):

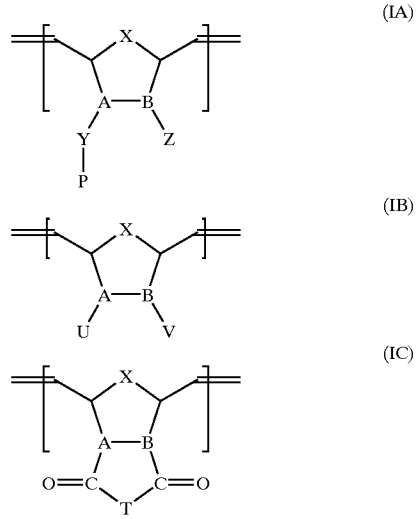

where X, A—B, Y, P, Z, U, V, T, $R^1$, $R^2$, $R^3$, $R^4$ and $R^5$ independently of one another have the following meanings:

X=$CH_2$ or O;

A—B=C—C or C=C;

Y=$CH_2O$, CO—O or COO—$R^1$—O, where $R^1$=substituted or unsubstituted $C_1$ to $C_5$ alkylene or oxyalkylene;

P=a polymerizable group $CH_2$=C($CH_3$)—CO—;

Z=H, COOH, substituted or unsubstituted $C_1$ to $C_{12}$ alkyl or COO$R^4$, where $R^4$=substituted or unsubstituted $C_1$ to $C_{12}$ alkyl or $C_6$ to $C_{14}$ aryl;

U=COOH or COO$R^5$, where $R^5$=substituted or unsubstituted $C_1$ to $C_{12}$ alkyl or $C_6$ to $C_{14}$ aryl;

V=H, COOH, $CH_2$—OH, O$R^2$ or CO—O$R^2$, where $R^2$=substituted or unsubstituted $C_1$ to $C_{12}$ alkyl or $C_6$ to $C_{14}$ aryl; and T=O, NH or NH$R^3$, where $R^3$=substituted or unsubstituted $C_1$ to $C_{12}$ alkyl or $C_6$ to $C_{14}$ aryl; and where the mole fraction a of the unit (IA), the mole fraction b of the unit (IB) and the mole fraction c of the unit (IC) are as follows:

a=0.05 to 1.0;
b=0 to 0.95; and
c=0 to 0.90.

2. Polymer according to claim 1, wherein the variables independently of one another have the following meaning:
X=$CH_2$ or O;
A—B=C—C;
Y=$CH_2O$ or CO—O—$R^1$—O;
$R^1$=$CH_2CH_2$ or $CH_2$—CHOH—$CH_2$;
P=$CH_2$=C($CH_3$)—CO;
Z=H or COOH;
$R^4$=$CH_3$, $C_2H_5$ or phenyl;
U=COOH;
$R^5$=$CH_3$, $C_2H_5$ or phenyl;
V=H or COOH;
$R^2$=$CH_3$ or $C_2H_5$;
T=O;
$R^3$=$CH_3$ or phenyl;
a=0.10 to 0.80;
b=0 to 0.80; and
c=0 to 0.60.

3. Process for the preparation of the polymer according to claim 1, wherein mixtures of optionally protected bicyclic compounds are subjected to a ring-opening methathesis polymerization in the presence of a catalyst, and subsequently any protective groups present are cleaved off, and wherein the mixtures contain
(a) the bicyclic compound of the general formula (II) and
(b) optionally the bicyclic compound of the general formula (III) and
(c) optionally the bicyclic compound of the general formula (IV)

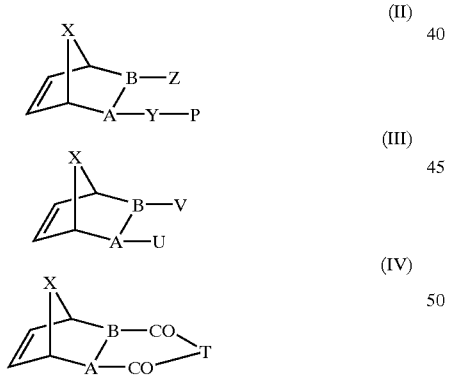

4. Composition containing the polymerizable polymer according to claim 1.

5. Composition according to claim 4, which is a cement, coating material, composite or adhesive.

6. Composition according to claim 4, which is a dental material.

7. Composition according to claim 4, which contains the polymerizable polymer in at least partially polymerized form.

8. Composition according to claim 4, which is a dental adhesive.

9. Functionalized and polymerizable polymer, which contains the following repeat units (IA), (IB) and (IC):

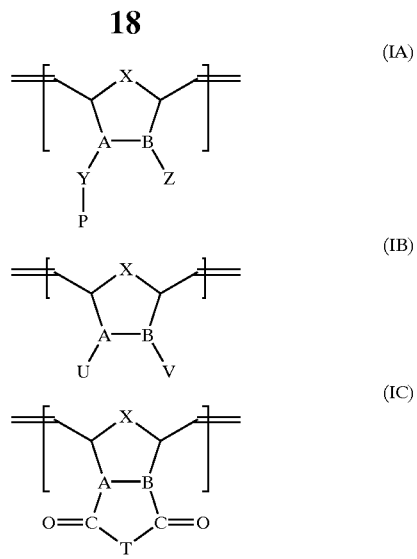

where X, A—B, Y, P, Z, U, V, T, $R^1$, $R^2$, $R^3$, $R^4$ and $R^5$ independently of one another have the following meanings:
X=$CH_2$ or O;
A—B=C—C or C=C;
Y=$CH_2O$, CO—O or COO—$R^1$—O, where $R^1$=substituted or unsubstituted $C_1$ to $C_5$ alkylene or oxyalkylene;
P=a polymerizable group of $CH_2$=CH—CO—, $CH_2$=C($CH_3$)—CO—, $CH_2$=CH—$CH_2$— or $CH_2$=CH—$C_6H_5$—$CH_2$—;
Z=H, COOH, substituted or unsubstituted $C_1$ to $C_{12}$ alkyl or COO$R^4$, where $R^4$=substituted or unsubstituted $C_1$ to $C_{12}$ alkyl or $C_6$ to $C_{14}$ aryl;
U=COOH or COO$R^5$, where $R^5$=substituted or unsubstituted $C_1$ to $C_{12}$ alkyl or $C_6$ to $C_{14}$ aryl;
V=H, COOH, $CH_2$—OH, O$R^2$ or CO—O$R^2$, where $R^2$=substituted or unsubstituted $C_1$ to $C_{12}$ alkyl or $C_6$ to $C_{14}$ aryl; and
T=O, NH or NH$R^3$, where $R^3$=substituted or unsubstituted $C_1$ to $C_{12}$ alkyl or $C_6$ to $C_{14}$ aryl; and
where the mole fraction a of the unit (IA), the mole fraction b of the unit (IB) and the mole fraction c of the unit (IC) are as follows:
a=0.05 to 1.0;
b=above 0 and up to 0.80; and
c=0 to 0.90.

10. A dental material comprising:
(1) the functionalized and polymerizable polymer according to claim 9, and
(2) a monofunctional or polyfunctional (meth)acrylate.

11. The dental material according to claim 10, wherein said polymer is present in an amount of from 0.1 to 60% by weight of the dental material.

12. The dental material according to claim 10, wherein said dental material is a light-curing glass ionomer cement or dentine adhesive.

13. The dental material according to claim 10, which contains the polymerizable polymer in at least partially polymerized form.

14. The dental material according to claim 12, which contains the polymerizable polymer in at least partially polymerized form.

15. A dental material comprising:
(1) the functionalized and polymerizable polymer according to claim 9, and
(2) a filler or reactive filler.

* * * * *

UNITED STATES PATENT AND TRADEMARK OFFICE
CERTIFICATE OF CORRECTION

PATENT NO.   : 6,479,592 B2
DATED        : November 12, 2002
INVENTOR(S)  : Rheinberger et al.

It is certified that error appears in the above-identified patent and that said Letters Patent is hereby corrected as shown below:

<u>Title page,</u>
Item [73], Assignee, delete "DE" in the Assignee's address so it reads -- Liechtenstein --

Signed and Sealed this

Ninth Day of September, 2003

JAMES E. ROGAN
*Director of the United States Patent and Trademark Office*